United States Patent [19]

Takehara et al.

[11] Patent Number: 5,847,205

[45] Date of Patent: Dec. 8, 1998

[54] METHOD FOR PRODUCING HOMOCYSTINE

[75] Inventors: Jun Takehara; Shuji Ichikawa; Hiroshi Iwane, all of Inashiki-gun, Japan

[73] Assignee: Mitsubishi Chemical Corporation, Tokyo, Japan

[21] Appl. No.: 975,854

[22] Filed: Nov. 21, 1997

[30] Foreign Application Priority Data

Nov. 25, 1996 [JP] Japan ................................ 8-313572
May 29, 1997 [JP] Japan ................................ 9-139799

[51] Int. Cl.⁶ ................................................ C07C 315/00
[52] U.S. Cl. .................................................... 562/556
[58] Field of Search ............................................. 562/556

[56] References Cited

U.S. PATENT DOCUMENTS 4,550,199  10/1985  Karrenbauer et al. ................... 562/556
4,550,200  10/1985  Karrenbauer et al. ................... 562/556

OTHER PUBLICATIONS

L.W. Butz et al. The Formation of a Homologue of Cystine by the Decomposition of Methione with Sulfuric Acid, J. Biol. Chem. vol. 99 (1932), pp. 135–142.

K. Osono et al, Amino Acids from an Amino Acid, in Boiling 20 % HCl, Nagasaki Igakkai Zassi, vol. 30, No. 1 (1955), pp. 156–161.

*Primary Examiner*—Gary Geist
*Assistant Examiner*—Brian J. Davis
*Attorney, Agent, or Firm*—Dilworth & Barrese

[57] ABSTRACT

Homocystine is produced by heating methionine in the presence of sulfuric acid and a hydrogen halide.

9 Claims, No Drawings

METHOD FOR PRODUCING HOMOCYSTINE

FIELD OF THE INVENTION

This invention relates to a method for the production of homocystine. Homocystine and its reduction-cyclization product (i.e., homocysteine thiolactone) are useful as intermediates for synthesizing various organic compounds including pharmaceutical drugs and agricultural chemicals.

BACKGROUND OF THE INVENTION

With regard to the method for the production of DL-homocystine, methods are known in which DL-methionine is used as the starting material, which is industrially synthesized using the general purpose industrial product acrolein as the raw material and is inexpensive and readily available. For example, a method has been reported in J. Biol. Chem., 99, 135 (1932–33), in which DL-methionine is heated in a large excess of concentrated sulfuric acid. This method, however, is not desirable as an industrial production method for the reasons that the yield of DL-homocystine is limited to 50% due to formation of a large amount of the by-product dimethylsulfonium salt (methionine-S-methylsulfonium sulfate), a large amount of a base is required for the neutralization of sulfuric acid after the reaction and when D-methionine or L-methionine is used as the starting material, there is a reduction of optical purity due to the necessity of employing a high temperature to compensate for the low reaction rate.

In addition, another method has been reported in which DL-methionine is reduced with metallic sodium in liquid ammonia to provide DL-homocysteine which is subsequently oxidized to produce DL-homocystine (West German Patent Nos. 3309761 and 2547672). This method, however, is not desirable as an industrial production method since it uses liquid ammonia and metallic sodium which cannot be handled easily and that it requires multiple reaction steps.

The present invention contemplates providing an industrially advantageous production method by which high quality homocystine is produced with high safety and low cost using methionine as the starting material.

SUMMARY OF THE INVENTION

In accordance with the present invention, a method has been discovered which accelerates the reaction of methionine with sulfuric acid and decomposes the by-product dimethylsulfonium salt into methionine. In particular, it has been found that by introducing a hydrogen halide into the reaction system, conversion of the dimethylsulfonium salt into methionine proceeds with high efficiency so that continued reaction of the thus-formed methionine with sulfuric acid renders possible not only high yield production of the intended homocystine but also improvement of the reaction rate, and D- and/or L-homocystine can be obtained without disadvantage to its optical purity when D- or L-methionine is used as the material.

Accordingly, the present invention provides a method for the production of homocystine which comprises heating methionine in the presence of sulfuric acid and a hydrogen halide.

DETAILED DESCRIPTION OF THE INVENTION

The following describes the method of the present invention in more detail.

Methionine

Although any of the racemic and optically active forms of methionine can be used as the starting material herein without regard to the method of production, the racemic mixtures are especially advantageous in that they are produced on an industrial scale, for example, by using acrolein as the material, effecting addition of methanethiol to the material and then subjecting the addition product to Strecker reaction and subsequent hydrolysis reaction.

Production Method

The reaction for producing homocystine is carried out by heating DL-methionine or D- and/or L-methionine together with sulfuric acid and a hydrogen halide. In this case, a solvent may be used or may not be used. With regard to the sulfuric acid, pure sulfuric acid or concentrated sulfuric acid of 10% by weight or more in concentration is used. The amount of sulfuric acid to be used is 0.5 mole or more, preferably 1 to 10 moles per 1 mole of methionine.

As the hydrogen halide, hydrogen chloride, hydrogen bromide, hydrogen iodide or the like, preferably hydrogen bromide, is used. Each of these hydrogen halides may be used in its gaseous form or as a hydrohalogenic acid of 20% by weight or more in concentration by allowing water to absorb the gas. The amount to be used is equivalent or more in molar ratio to methionine.

The heating temperature is within the range of from 60° to 150° C., preferably from 80° to 140° C. The reaction time varies depending on the heating temperature and amounts of sulfuric acid and hydrogen halide, but the reaction is substantially completed generally after 1 to 30 hours. In order to remove the sulfur dioxide and methyl halide formed, the reaction is preferably carried out with stirring in a stream of inert gas of, for example, nitrogen. Since the resulting homocystine formed after completion of the reaction is dissolved in the reaction solution in its sulfuric acid salt form, the free homocystine can be obtained easily by neutralizing the solution with a base such as sodium hydroxide aqueous solution or the like, and collecting the thus precipitated homocystine crystals by filtration and washing with water.

The method of the present invention may be illustrated by the following reaction scheme:

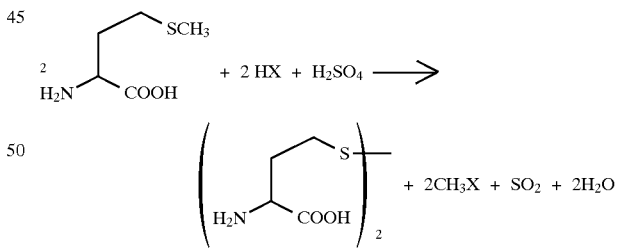

(In the above formula, X represents a halogen atom.)

According to the method of the present invention, homocystine can be obtained in high yield by the use of a hydrogen halide. As shown in the following reaction scheme, it is believed that the hydrogen halide reacts with a dimethylsulfonium salt formed by the reaction of methionine with sulfuric acid converting such salt into methionine.

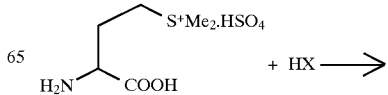

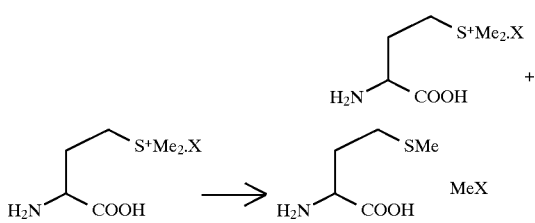

(In the above formula, Me represents a methyl group and X represents a halogen atom.)

The following examples further illustrate the present invention.

In the examples, the substances formed were analyzed quantitatively by an internal standard method using liquid chromatography, and conversion ratio and selectivity were calculated based on the following formulae.

Conversion ratio (%)=100×(mole of reacted material)/(mole of charged material)

Selectivity (%) = 100 × (mole of intended product (Note 1) × 2)/{mole of intended product (Note 1) × 2 + mole of by-products (Note 2)}

Note 1: homocystine sulfate
Note 2: methionine-S-methylsulfonium sulfate and homocystine sulfate

EXAMPLE 1

A 50 ml capacity glass reaction flask was charged with 5 g (33.56 mmol) of DL-methionine and 17.35 g (100.68 mmol) of 47% HBr aqueous solution together with a stirrer tip, 6.71 g (67.12 mmol) of concentrated sulfuric acid was added thereto with ice-cooling and then the contents were heated under reflux for 6 hours at 120° C. with stirring in a stream of nitrogen.

The reaction solution was analyzed by liquid chromatography. As a result, it was found that 5.65 g (15.44 mmol) of DL-homocystine sulfate and 0.49 g (2.68 mmol) of DL-homocysteine sulfate were formed. The conversion ratio was 100% and the selectivity was 92%.

Next, the reaction solution was neutralized with 10% sodium hydroxide aqueous solution while cooling, and the resulting precipitate was collected by filtration, washed with water and then dried to give 4.05 g of DL-homocystine. The yield based on DL-methionine was 90%.

COMPARATIVE EXAMPLE 1

A 50 ml capacity glass reaction flask was charged with 5 g (33.56 mmol) of DL-methionine, 30.20 g (302.04 mmol) of concentrated sulfuric acid and 16.4 g of water and then the contents were heated under reflux for 3.5 hours at 135° C. in a stream of nitrogen. The reaction solution was analyzed by liquid chromatography. As a result, it was found that 2.92 g (7.97 mmol) of DL-homocystine sulfate and 4.96 g (16.00 mmol) of DL-methionine-S-methylsulfonium sulfate were formed. The conversion ratio was 100% and the selectivity was 48%.

Next, the reaction solution was neutralized with 10% sodium hydroxide aqueous solution while cooling, and the resulting precipitate was collected by filtration, washed with water and then dried to give 1.93 g of DL-homocystine. The yield was 43%.

EXAMPLE 2

A 50 ml capacity glass reaction flask was charged with 5 g (33.56 mmol) of L-methionine and 5.78 g (33.56 mmol) of 47% HBr aqueous solution together with a stirrer tip, 6.71 g (67.12 mmol) of concentrated sulfuric acid was added thereto with ice-cooling and then the contents were heated for 9 hours at 100° C. with stirring in a stream of nitrogen.

The reaction solution was analyzed by liquid chromatography. As a result, it was found that 0.13 g (0.67 mmol) of L-methionine sulfate, 2.64 g (7.22 mmol) of L-homocystine sulfate and 4.25 g (13.72 mmol) of L-methionine-S-methylsulfonium sulfate were formed. The conversion ratio was 98% and the selectivity was 43%.

Next, the reaction solution was neutralized with 10% sodium hydroxide aqueous solution while cooling, and the resulting precipitate was collected by filtration, washed with water and then dried to give 1.84 g of L-homocystine. The yield based on L-methionine was 41%, and its optical purity was 99.7% or more.

COMPARATIVE EXAMPLE 2

A 100 ml capacity glass reaction flask made of glass was charged with 10 g (67.11 mmol) of L-methionine, 13.42 g (134.22 mmol) of concentrated sulfuric acid and 7.76 g of water, and then the contents were heated for 9 hours at 100° C. in a stream of nitrogen.

The reaction solution was analyzed by liquid chromatography. As a result, it was found that 3.59 g (18.12 mmol) of L-methionine sulfate, 1.06 g (2.9 mmol) of L-homocystine sulfate and 1.86 g (6 mmol) of L-methionine-S-methylsulfonium sulfate were formed. The conversion ratio was 16.6% and the selectivity was 49%.

According to the method of the present invention, homocystine can be obtained in high yield using methionine as the starting material which is industrially readily available. Since the reaction can be carried out under relatively mild conditions without using materials which are difficult to handle (e.g., liquid ammonia and the like), the method of the present invention is especially well adapted for industrial operation.

While the invention has been described in detail and with reference to specific embodiments thereof, it will be apparent to one skilled in the art that various changes and modifications can be made therein without departing from the spirit and scope thereof.

This application is based on Japanese patent application Hei-8-313572, filed on Nov. 25, 1996, and Hei-9-139799, filed on May 29, 1997, incorporated herein by reference.

What is claimed is:

1. A method for producing homocystine, which comprises heating methionine in the presence of sulfuric acid and a hydrogen halide.

2. The method according to claim 1, wherein the hydrogen halide is hydrogen bromide.

3. The method according to claim 1, wherein said methionine is DL-methionine and the homocystine produced is DL-homocystine.

4. The method according to claim 1, wherein said methionine is D-methionine and the homocystine produced is D-homocystine.

5. The method according to claim 1, wherein said methionine is L-methionine and the homocystine produced is L-homocystine.

6. The method according to claim 1, wherein said heating is carried out with stirring in a stream of inert gas.

7. The method according to claim 4, wherein the hydrogen halide is hydrogen bromide.

8. The method according to claim 5, wherein the hydrogen halide is hydrogen bromide.

9. The method according to claim 6, wherein the inert gas is nitrogen.

* * * * *